United States Patent
Wakuda

(10) Patent No.: US 12,382,844 B2
(45) Date of Patent: Aug. 5, 2025

(54) SUPERCONDUCTING MAGNET DEVICE, NMR DEVICE, AND MRI DEVICE

(71) Applicant: Hitachi High-Tech Corporation, Tokyo (JP)

(72) Inventor: Tsuyoshi Wakuda, Tokyo (JP)

(73) Assignee: HITACHI HIGH-TECH CORPORATION, Tokyo (JP)

(*) Notice: Subject to any disclaimer, the term of this patent is extended or adjusted under 35 U.S.C. 154(b) by 0 days.

(21) Appl. No.: 18/281,342

(22) PCT Filed: Aug. 1, 2022

(86) PCT No.: PCT/JP2022/029438
§ 371 (c)(1),
(2) Date: Sep. 11, 2023

(87) PCT Pub. No.: WO2023/037792
PCT Pub. Date: Mar. 16, 2023

(65) Prior Publication Data
US 2024/0155951 A1  May 9, 2024

(30) Foreign Application Priority Data
Sep. 7, 2021 (JP) .................. 2021-145556

(51) Int. Cl.
*H10N 60/84* (2023.01)
*G01R 33/38* (2006.01)
(Continued)

(52) U.S. Cl.
CPC ......... *H10N 60/84* (2023.02); *G01R 33/3804* (2013.01); *G01R 33/3815* (2013.01); *H02H 7/001* (2013.01); *H01F 6/02* (2013.01)

(58) Field of Classification Search
CPC .. A61B 5/055; G01R 33/288; G01R 33/3804; G01R 33/3815; H01F 6/02; H02H 7/001; H10N 60/202
(Continued)

(56) References Cited

U.S. PATENT DOCUMENTS 4,559,576 A      12/1985  Ries et al.
2002/0171520 A1*  11/2002  Yoshikawa ........ G01R 33/3815
                                                        335/216
(Continued)

FOREIGN PATENT DOCUMENTS

JP       59-144106 A     8/1984
JP       07-142773 A     6/1995
(Continued)

OTHER PUBLICATIONS

M Breschi, et al., "Analysis of quench in the NHMFL REBCO prototype coils for the 32T Magnet Project", Superconductor Science and Technology, 29, (5) May 2016, 055002.
(Continued)

*Primary Examiner* — Kevin J Comber
(74) *Attorney, Agent, or Firm* — MATTINGLY & MALUR, PC

(57) ABSTRACT

There is provided a superconducting magnet device including: a superconducting coil (main coil) in which a superconducting wire material is wound; and a persistent current switch (PCS) electrically connected in parallel with the superconducting coil with respect to an excitation power supply for the superconducting coil, in which the excitation power supply is electrically connected to the superconducting coil and the persistent current switch via a current lead, the persistent current switch is provided with a PCS heater and a PCS heater power supply for transitioning from a super-conduction state to a normal conduction state, and a current supplied to the PCS heater winding from the PCS heater power supply flows to the heater via at least a part of the current lead.

16 Claims, 7 Drawing Sheets

(51) Int. Cl.
*G01R 33/3815* (2006.01)
*H02H 7/00* (2006.01)
*H01F 6/02* (2006.01)

(58) Field of Classification Search
USPC .......................................................... 361/19
See application file for complete search history.

(56) References Cited

U.S. PATENT DOCUMENTS

| | | | | |
|---|---|---|---|---|
| 2004/0027737 A1* | 2/2004 | Xu | ......................... | H02H 7/001 |
| | | | | 361/19 |
| 2006/0158795 A1* | 7/2006 | Tsuchiya | ................ | H02H 7/001 |
| | | | | 361/19 |
| 2006/0279387 A1* | 12/2006 | Nemoto | ................... | H01F 6/04 |
| | | | | 335/216 |
| 2013/0234815 A1* | 9/2013 | Milward | ................ | H01F 6/006 |
| | | | | 335/216 |
| 2016/0343491 A1* | 11/2016 | Miyazoe | ................... | H01F 6/06 |

FOREIGN PATENT DOCUMENTS

| | | |
|---|---|---|
| JP | 2003-197418 A | 7/2003 |
| JP | 2006-073571 A | 3/2006 |
| JP | 2010-147370 A | 7/2010 |

OTHER PUBLICATIONS

Weijers et al.: "The NHMFL 32T superconducting magnet", 2017.
International Search Report PCT/JP2022/029438 dated Oct. 25, 2022.

* cited by examiner

[FIG. 1]
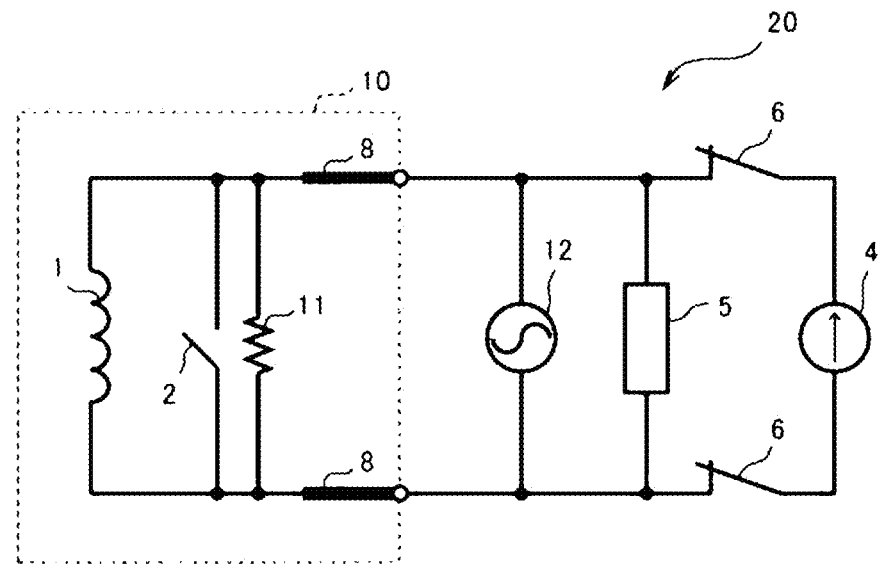
[FIG. 2]
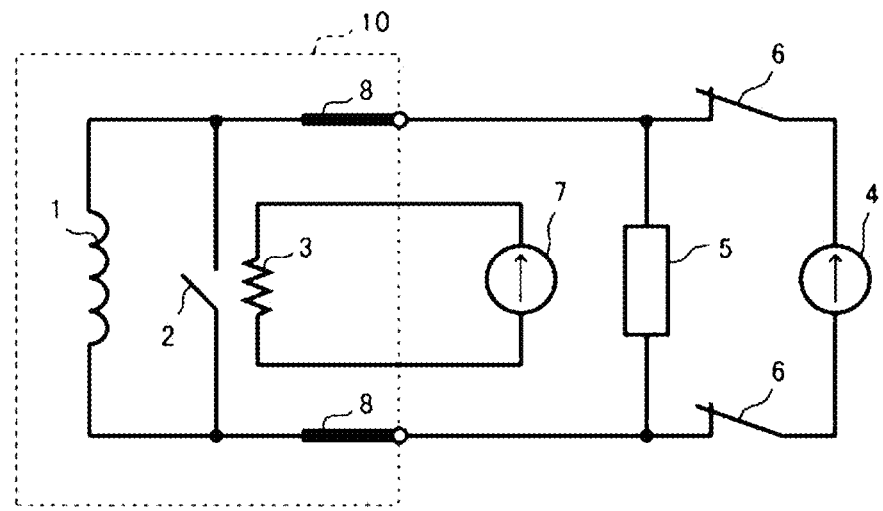

[FIG. 3]
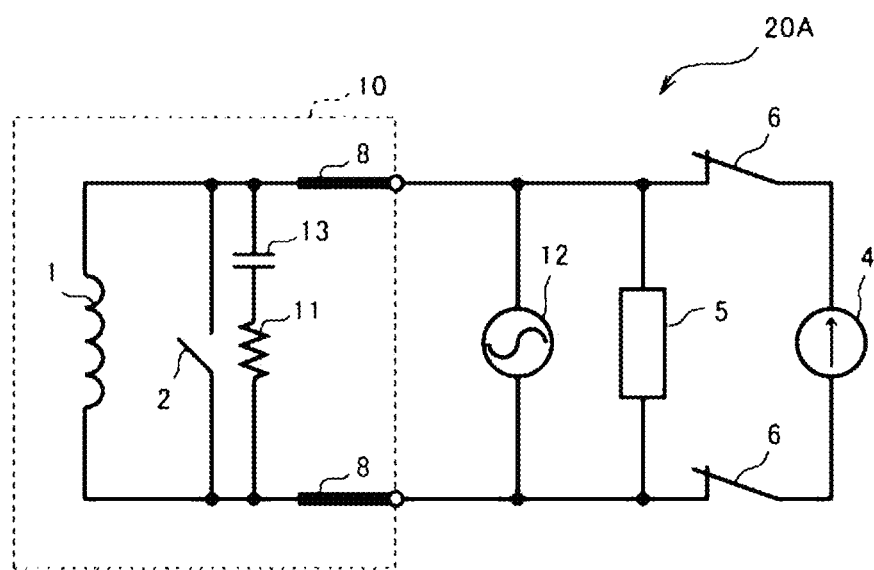

[FIG. 4]
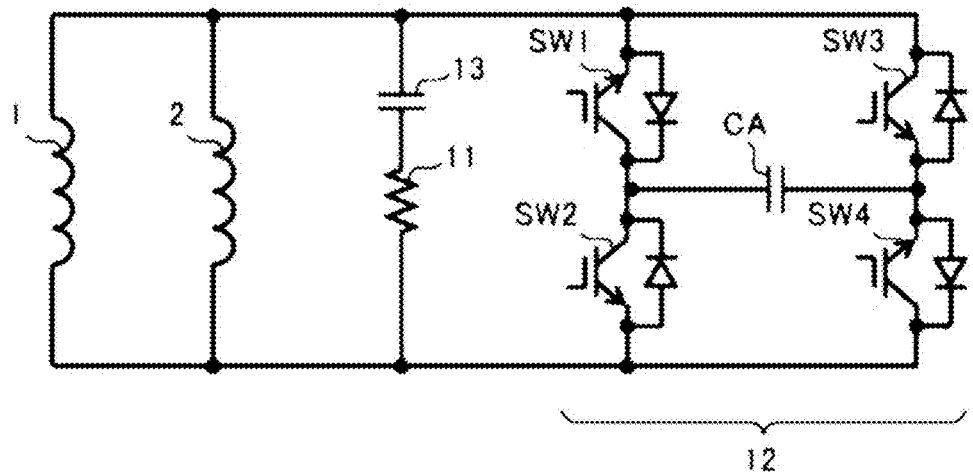

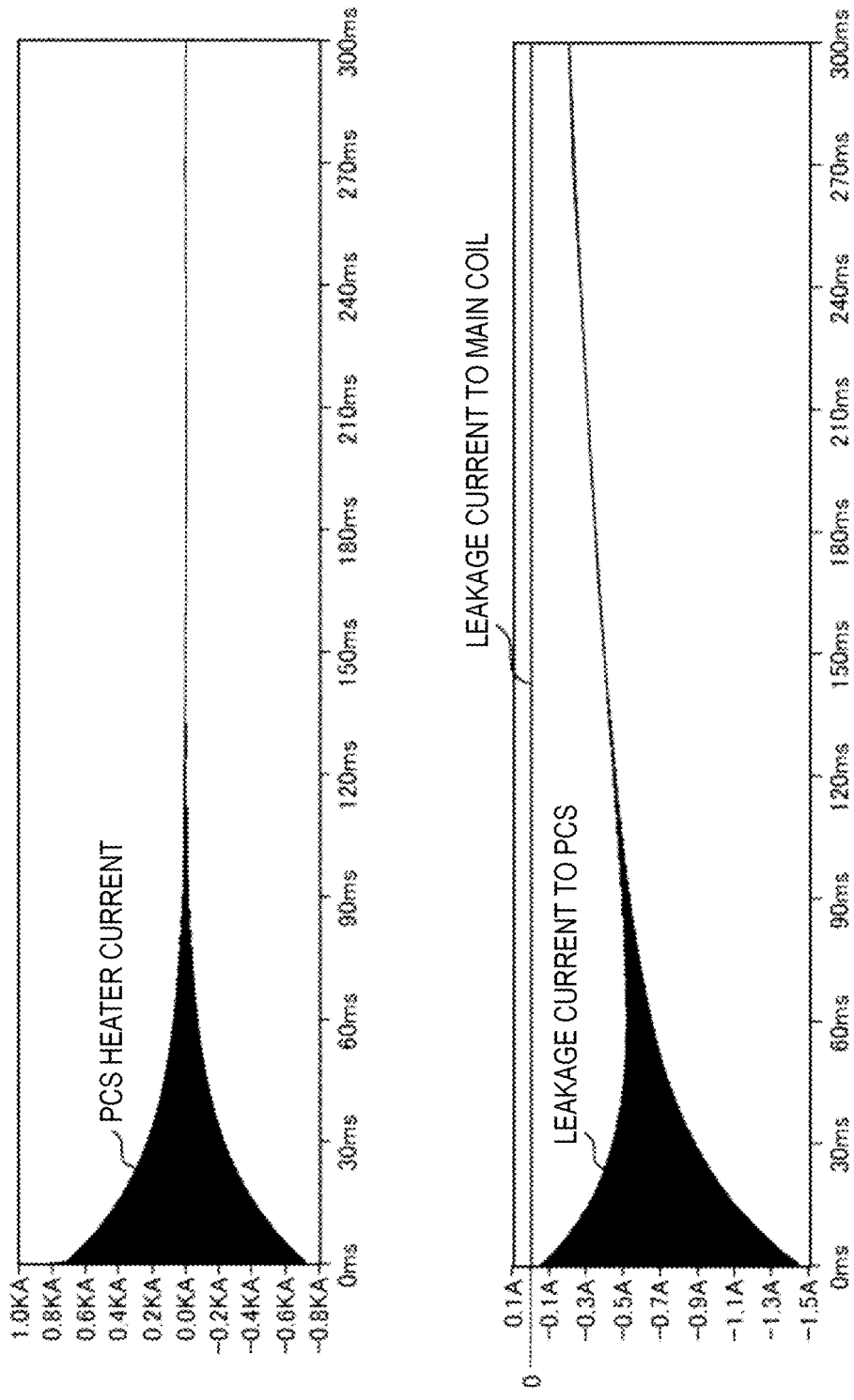
[FIG. 5]

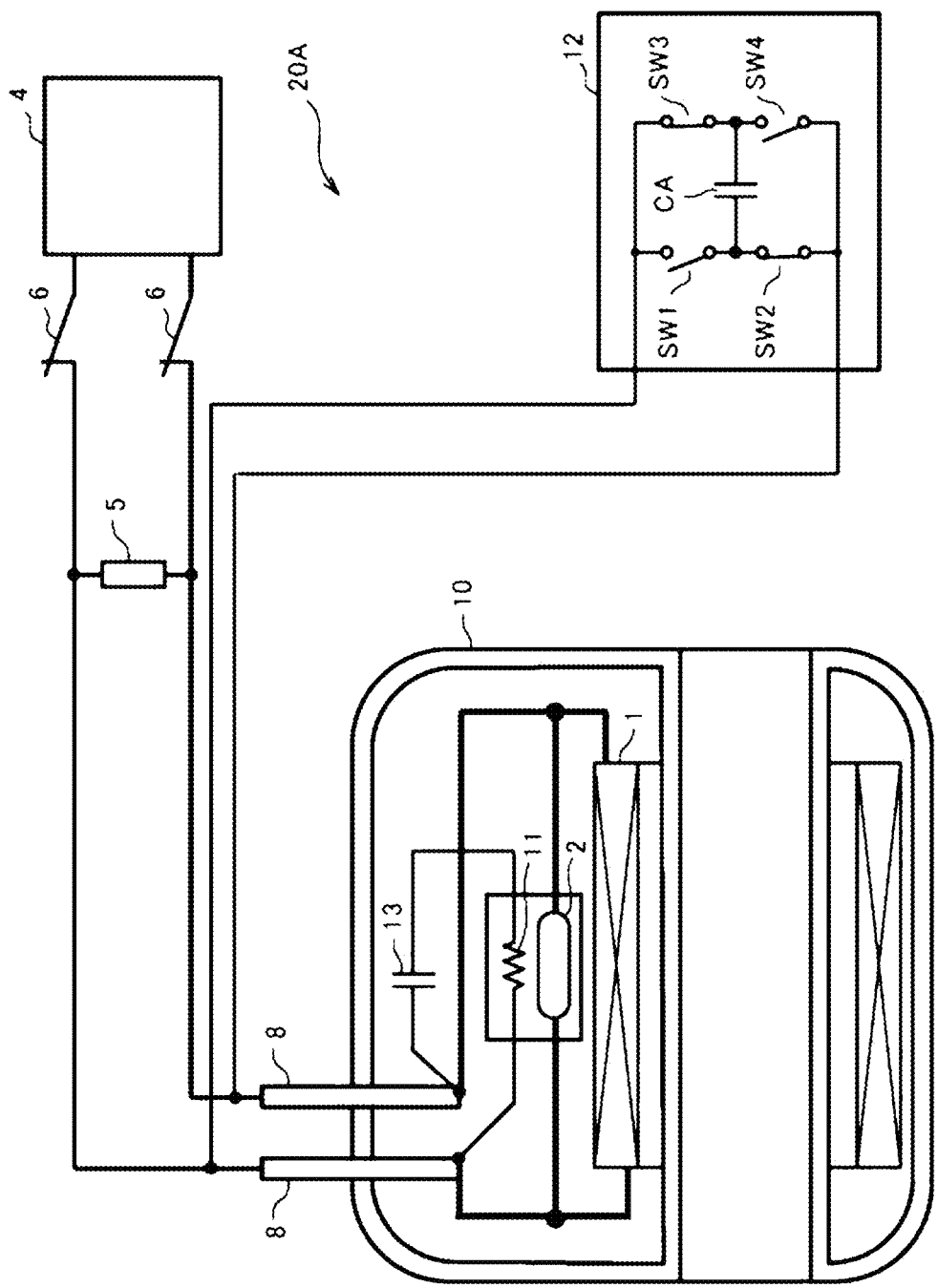
[FIG. 6]

[FIG. 7]
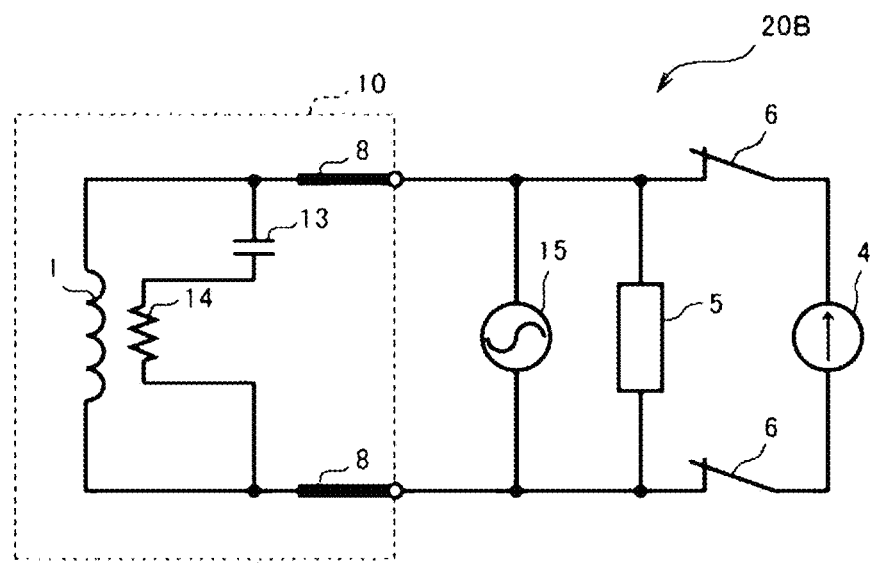

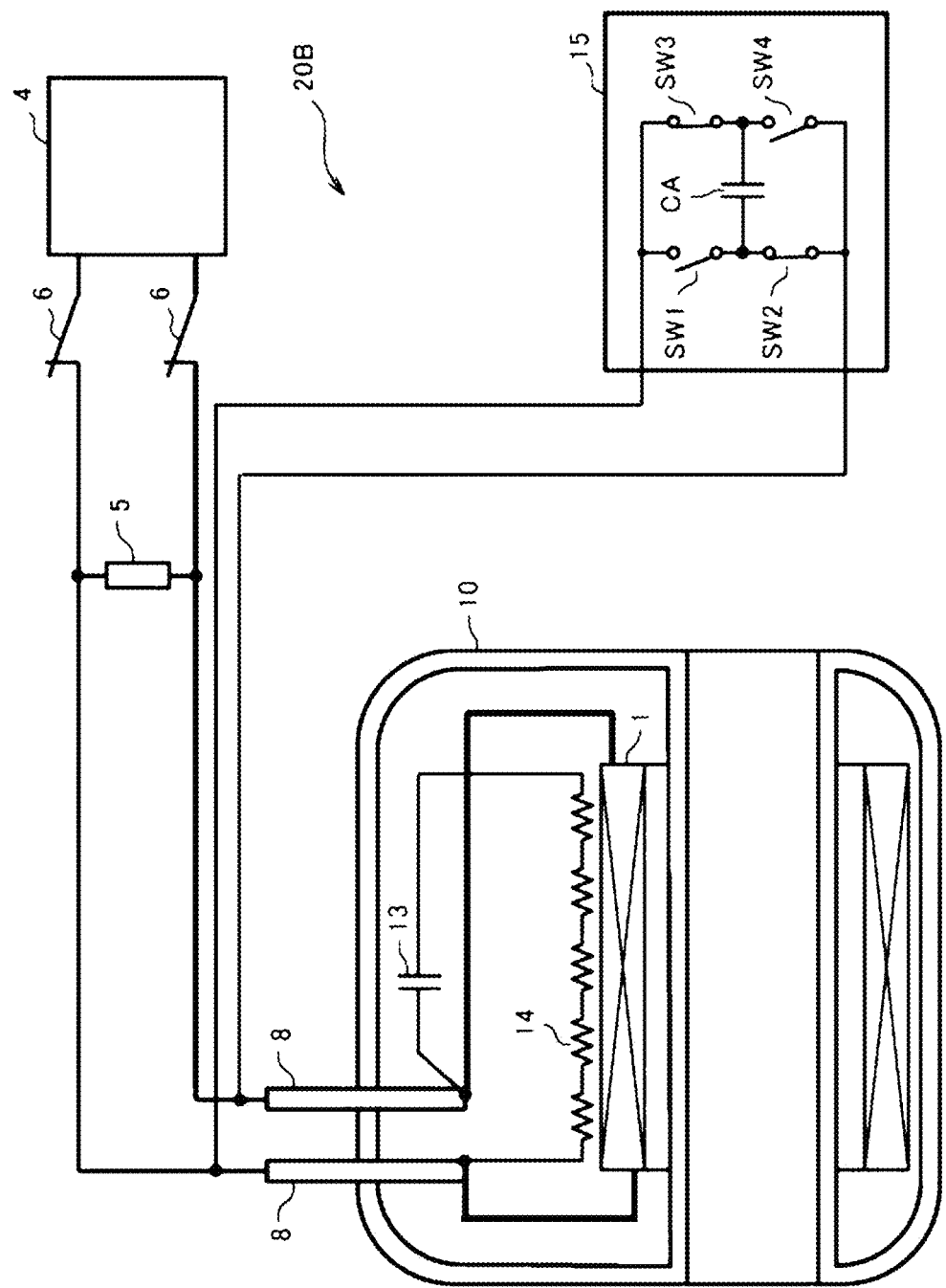
[FIG. 8]

SUPERCONDUCTING MAGNET DEVICE, NMR DEVICE, AND MRI DEVICE

TECHNICAL FIELD

The present invention relates to a superconducting magnet device that generates a high magnetic field and utilizes the magnetic field, and more particularly to a superconducting magnet device that requires high speed breaking of a magnet and performs a breaking operation with a heater.

BACKGROUND ART

Superconducting magnets can generate a higher magnetic field than permanent magnets or normal conducting electromagnets, and thus the superconducting magnets are used as ultra-high magnetic field magnets for research, magnets for analysis device such as nuclear magnetic resonance (NMR), and magnets for medical magnetic resonance imaging (MRI), which cannot be realized with permanent magnets or the like.

Metallic NbTi, $Nb_3Sn$, and the like have been used as practical superconducting materials, but such materials are called low temperature superconductor (LTS) and are used in a temperature range using liquid helium. On the other hand, research for practical application of high temperature superconductor (HTS) exhibiting superconducting properties at a high critical temperature has progressed, and various HTS magnets have been developed in recent years. As a high temperature superconductor, REBCO containing rare earth elements (such as Y and Gd), copper oxide superconducting materials such as BSCCO containing Bi, and $MgB_2$, which is a metallic material, are being put to practical use.

Since superconducting magnets are used to allow a larger current than normal conducting conductors to flow by taking advantage that a direct current electric resistance is zero, the quenching phenomenon, in which a super-conduction state is suddenly transitioned to a normal conduction state, is generally avoided. High temperature superconductors have a high critical temperature, and using such property, the high temperature superconductors are operated in a temperature range in which the specific heat is much higher than that of the liquid helium temperature range, and thus, a quench energy margin is much larger than that of the LTS magnet with respect to quench due to heat input to the heat energy into the superconducting magnet due to disturbance.

An advantage of the HTS is that a quench resistance is high, but such property may be a disadvantage. Magnets for MRI and the like operate in a persistent current mode to realize magnetic field stability. When operating in the persistent current mode, the circuit of the superconducting magnet must have no electric resistance, and the circuit forms a superconducting loop with zero resistance. Since a current cannot flow into the superconducting loop, the persistent current mode magnet is equipped with a switch called a persistent current switch (PCS) that can switch from a super-conduction state and a normal conduction state (resistive state).

The persistent current switch is configured by a super-conducting wire material and is generally provided with a heater for transitioning from the super-conduction state to the normal conduction state. The resistive state (that is, switch off) is realized by supplying energy to the heater to raise the temperature of the persistent current switch, and the super-conduction state (that is, switch on) is realized by turning off the heater and lowering the temperature.

PTL 1 discloses a general persistent current mode circuit configured by a superconducting coil, a persistent current switch, a protection circuit, and an excitation power supply, and the persistent current switch is turned on and off by a heater for opening and closing the persistent current switch. A protection resistor is used as a heater for turning off the persistent current switch.

MRI operated in the persistent current mode requires a function to turn off the magnetic field quickly in emergency. By putting the PCS in the resistive state (switch off), it is possible to extract the energy of the magnet and demagnetize the magnetic field, but for emergency demagnetization, it is necessary to quickly turn off the switch. In the HTS magnet operated in the persistent current mode, the HTS wire material is also used for the PCS winding, and thus it is difficult to switch the PCS into the resistive state in a short period of time.

Once the superconducting magnet is quenched, the HTS magnet tends to burn out more easily than the LTS magnet. This is because the HTS has a property that it is difficult to quench, and thus the normal conducting region does not expand quickly, and energy stored in the magnet is concentrated in a local region where quenching occurs and is converted into heat, forming a hot spot.

To prevent burnout caused by the hot spot, there is a magnet protection method in which a heater called a quench heater is installed in the superconducting coil, and when the quench occurs, the superconducting region is broadly transitioned to the normal conduction state to expand the resistance region. It is difficult to expand the resistance region by the quench heater because of the high quench resistance of the HTS magnet.

In NON PTL 1 and NON PTL 2, a quench heater is inserted between pancake coil layers in a magnet configured by laminating pancake coils wound with an oxide superconducting tape wire material. NON PTL 2 shows a battery bank for driving the quench heater.

CITATION LIST

Patent Literature

PTL 1: JPH07-142773A

Non Patent Literature

NON PTL 1: M Breschi et al.: "Analysis of quench in the NHMFL REBCO prototype coils for the 32T Magnet Project", May 2016 Superconductor Science and Technology 29(5) 055002

NON PTL 2: HW Weijers et al.: "The NHMFL 32T super-conducting magnet", https://indico.cern.ch/event/659554/contributions/2708372/attachments/1525993/2386079/3P1-01_Huub_Weijers_Room_1.pdf

SUMMARY OF INVENTION

Technical Problem

In superconducting magnets using superconductors of the related art using Nb-based materials (NbTi, $Nb_3Sn$), the critical temperature of such materials is low, and since such materials are used at the liquid helium temperature, which has a small specific heat, a small heater heat input can easily cause a quench. Quench buds (normal conducting region) generated by the heater are rapidly expanded by Joule heat generated by the current flowing through the coil, and the entire superconducting magnet can be switched to the resistive state.

On the other hand, HTS magnets have a high critical temperature as a material characteristic and are used in a temperature range having a much higher specific heat, and thus, the amount of heat to induce quenching becomes much larger, and the expansion speed of the normal conducting region (called quench propagation speed) is slow. To form a large resistance region in the superconducting coil, it is necessary to install heaters over a wide region and to supply heater energy to raise the temperature of the region. Therefore, HTS magnets require a large amount of energy for normal conduction transition to perform high speed breaking, and a heater power supply device with a high power output (W) is required for supplying instantaneous energy.

Since it is wasteful to equip a large capacitance power supply device for the quench heater and always keep the device in a standby state, it is rational to use a capacitor bank for the power supply for the heater. A simple heater power supply can be configured by charging energy for raising the temperature of the superconducting winding portion by a predetermined amount in the capacitor bank and discharging the energy when necessary.

The heater energy release time is determined by a time constant $\tau(=RC)$ determined by a capacitance C of the capacitor bank and an electric resistance R including a resistance of the heater and a heater energizing circuit resistance. A time constant of 20 to 30 msec is required because it is necessary to release all the energy of the capacitor bank in a very short time (0.1 sec) for high speed breaking. Since HTS magnets require much larger energy than LTS magnets, the required capacitor bank capacitance is larger, and thus the capacity C is larger.

In the heater circuit, the superconducting coil is installed in an extremely low temperature inside the cryostat, and thus, to reduce the heat input from outside via the heater energizing circuit, a conductor such as constantan with high thermal resistance (thus, high electric resistance) is used, and the electric resistance of the heater energizing circuit cannot be reduced. Therefore, when using the capacitor bank, HTS magnets do not provide a high speed breaking operation.

The present invention is an invention for solving the above-described problems, and an object thereof is to provide a heater device capable of transitioning a superconducting winding to a normal conduction state at high speed, and a superconducting magnet device capable of high speed breaking of the superconducting magnet or prevention of burnout of the superconducting winding.

Solution to Problem

To achieve the above object, there is provided a superconducting magnet device including: a superconducting coil in which a superconducting wire material is wound; and a persistent current switch electrically connected in parallel with the superconducting coil with respect to an excitation power supply for the superconducting coil, in which the excitation power supply is electrically connected to the superconducting coil and the persistent current switch via a current lead, the persistent current switch is provided with a heater and a heater driving power supply for transitioning from a super-conduction state to a normal conduction state, and a current supplied to the heater from the heater driving power supply flows to the heater via at least a part of the current lead. Other aspects of the present invention will be described in embodiments below.

Advantageous Effects of Invention

According to the present invention, there is provided a heater device capable of transitioning a superconducting winding to a normal conduction state at high speed, thereby enabling high speed breaking of a superconducting magnet or prevention of burnout of the superconducting winding.

BRIEF DESCRIPTION OF DRAWINGS

FIG. 1 is a circuit diagram showing a basic configuration of a persistent current mode operation magnet according to a first embodiment.

FIG. 2 is a circuit diagram showing a basic configuration of a general persistent current mode operation magnet.

FIG. 3 is a circuit diagram showing a superconducting magnet device according to the first embodiment.

FIG. 4 is an explanatory diagram showing a circuit simulation model according to the first embodiment.

FIG. 5 is a time change diagram of a current showing results of the circuit simulation model according to the first embodiment.

FIG. 6 is a configuration diagram showing the superconducting magnet device according to the first embodiment.

FIG. 7 is a circuit diagram showing a superconducting magnet device according to a second embodiment.

FIG. 8 is a configuration diagram showing the superconducting magnet device according to the second embodiment.

DESCRIPTION OF EMBODIMENTS

An embodiment of the present invention will be described. However, the present invention is not limited to the embodiments described here, and appropriate combinations and improvements are possible without changing the gist of the invention.

First Embodiment

<Construction of Persistent Current Mode Magnet>

First, with reference to FIG. 2, a basic configuration of a general persistent current mode operation magnet and problems thereof will be described.

FIG. 2 is a circuit diagram showing a basic configuration of a general persistent current mode operation magnet. FIG. 2 shows a typical excitation circuit for a persistent current mode operation magnet with a central magnetic field strength of 1.5 T wound with $MgB_2$. The magnet has an operation current of 250 A, is cooled by a conduction cooling method, and has an storedenergy of 3 MJ.

A main coil 1 (superconducting coil) is connected to an excitation power supply rated at 300 A, and a PCS 2 (persistent current switch) is connected in parallel with the main coil 1 for a persistent current mode operation. A 10Ω protection resistor 5 is installed outside a cryostat 10 such that most (90% or more) of the stored energy of the magnet can be recovered outside the cryostat 10 during quenching.

In a general commercially available persistent current mode magnet, after the persistent current mode operation is established to reduce the amount of heat input to the cryostat 10, a power lead 8 for supplying a current to the magnet is drawn out. However, in the configuration of the magnet, the power leads remain installed to recover the energy with the external protection resistor 5.

The PCS 2 is wound with a $MgB_2$ superconducting wire material, and is installed to be thermally coupled with a PCS heater winding 3 (heater) for a switch operation. A PCS heater power supply 7 is provided for driving the heater. In general, the PCS heater winding 3 and the PCS heater power supply 7 are connected by a constantan wire with high thermal resistance to reduce heat penetration into the cryostat 10.

The PCS 2 has zero resistance during persistent current mode operation, but is designed to have a resistance of 100 to 300Ω when the PCS 2 is turned off, to recover most of the storedenergy in an external protection resistor when a main coil quench occurs or emergency breaking occurs. To turn off the PCS 2, it is necessary to supply energy that is at least 1500 to 4000 J. The off-time target specification for PCS 2 of the magnet is 0.1 seconds, and here, a standby power supply of 15 kW to 40 kW is required to drive the heater. Since it is wasteful to keep such a large power supply on standby for the heater, a capacitor bank with a total capacitance of 47000 μF is charged with 300 to 600 V and kept on standby.

<Low Resistance Heater Circuit>

Energy supply from the capacitor bank to the heater circuit is performed passively, and the time required for energy supply is governed by a time constant $\tau=RC$ determined by a capacitance C of the capacitor bank and an electric resistance R of the heater circuit. Since it takes 3 to 4 times the time constant to finish supplying almost all the energy of the capacitor bank to the heater, the required circuit time constant is 25 to 33 msec.

Therefore, the electric resistance of the heater circuit (including the heater) is approximately 0.5Ω. Since the energy supplied from the capacitor is distributed according to a ratio of the electric resistance of the heater and an electric resistance of an intermediate path, the electric resistance of the intermediate path must be sufficiently smaller (for example, 10% or less) than the electric resistance of the heater.

Since it is desired to reduce the amount of heat penetration into the cryostat 10, it is preferable to use a material having a large thermal resistance as the conductor material of the heater circuit. When the amount of heat penetration is not a concern, the heater excitation circuit is configured with a copper wire or the like having a small electric resistance (thus, small thermal resistance).

To reduce the thermal resistance from the heater circuit, a material with high thermal resistance (thus, high electric resistance) such as constantan is usually selected. However, since the electric resistance extraordinarily increases, an energy supply time constant greatly increases, and the time constant of 25 to 33 msec cannot be realized. In the embodiment, the problem of the related art is solved by changing the circuit configuration.

FIG. 1 is a circuit diagram showing a basic configuration of a persistent current mode operation magnet according to a first embodiment. To reduce the amount of heat penetration, the heater excitation circuit is not provided separately, and a part of the excitation circuit for the main coil 1 is used in common to configure the heater excitation circuit as shown in FIG. 1. Since a large current is energized to the main coil 1 of the superconducting magnet device 20 during excitation, the electric resistance of the current lead 8 is sufficiently small, making it possible to realize a short time constant.

In FIG. 1, the excitation power supply 4 is electrically connected to the main coil 1 (superconducting coil) and the PCS 2 (persistent current switch) via the current lead 8, and the PCS 2 includes a PCS heater winding 11 (heater) and a PCS heater power supply 12 (heater driving power supply) for transitioning from a super-conduction state to a normal conduction state. A current supplied to the heater from the heater driving power supply is configured to flow via at least a part of the current lead 8 to the heater. The PCS heater power supply 12 is AC driven. Details will be described later.

By using a part of the excitation circuit of the main coil 1, the amount of heat input from the heater excitation circuit can be made zero, and the load on the refrigerator can be reduced. The heater and the heater excitation circuit are for turning off the PCS 2 at high speed, and the heater and the heater power supply for maintaining the PCS 2 in the off state to excite the superconducting coil 1 are mounted separately (not shown).

<Heater AC Drive>

Since a circuit breaker 6 disconnects the excitation power supply 4 from the circuit during high speed breaking, when looking at the main coil 1 (superconducting coil) side from the PCS heater power supply 12, the main coil 1 is connected to the PCS heater power supply 12, and the PCS 2 (PCS superconducting winding) and the PCS heater winding 11 (heater) are connected in parallel to the excitation circuit of the main coil 1. Therefore, the energy (current) supplied from the capacitor bank is distributed according to each impedance.

When an impedance of the heater (AC resistance+DC resistance of heater) is sufficiently larger than an impedance of the superconducting winding portions of the main coil 1 and the PCS 2, the shunting reduces the current flowing through the heater (that is, supplied energy). Since an inductance of the superconducting winding of the PCS 2 is sufficiently smaller than an inductance of the main coil 1, current distribution between the PCS superconducting winding and the heater is the main part.

The PCS superconducting windings in the PCS of the related art are generally non-inductive windings and have almost zero inductance. However, in the embodiment, the resistance of the heater is 0.5Ω, and the heater energy supply time constant is not short enough. Therefore, to prevent shunting, the PCS superconducting winding must be designed to have some inductance. In the magnet of the embodiment, the inductance of the PCS superconducting winding is set to approximately 0.01 H.

To make the shunting almost zero, it is necessary to supply energy at a faster current change speed. As a configuration for such purpose, a full bridge is configured in the capacitor bank with semiconductor switching elements or the like, and the purpose is realized by switching a voltage polarity of the capacitor bank as seen from the heater sufficiently faster than the energy supply time constant.

<Blocking Capacitor>

The magnet of the embodiment is designed to increase the energy recovery speed by increasing the resistance value of the external protection resistor (for example, 10Ω) to prevent burning of the main coil during quenching. When the electric resistance of the PCS heater winding 11 (heater) is less than that of the protection resistor, a current will flow through the heater resistor rather than the external protective resistor during the energy recovery process, such that most of the energy is recovered by the heater. Measures to prevent such result are necessary.

FIG. 3 is a circuit diagram showing a superconducting magnet device 20A according to the first embodiment. To prevent most of the energy from being recovered by the heater, a blocking capacitor 13 may be installed in the heater circuit such that a DC current does not flow, as shown in FIG. 3.

Although it is preferable to drive the heater with a DC power supply to prevent the shunting, the heater cannot be driven with a direct current when the blocking capacitor 13 is disposed, and thus, AC drive with a full bridge is essential. Since the impedance of the blocking capacitor 13 can be regarded as almost zero for a sufficiently fast AC current, the impedance does not affect the heater operation.

<Circuit Simulation Model>

FIG. 4 is an explanatory diagram showing a circuit simulation model according to the first embodiment. The PCS heater power supply 12 is simulated by a capacitor bank CA and a full bridge circuit of switching elements (switches SW1, SW2, SW3, and SW4). In the embodiment, the switching speed is set to 10 kHz. However, the switch operation allows the capacitor bank CA configured by DC voltage to be regarded as an AC power supply, and as the current change speed increases, the impedance of the PCS superconducting winding of the PCS 2 increases significantly, making it possible to prevent shunting. Insulated gate bipolar transistor (IGBT), metal oxide semiconductor field effect transistor (MOSFET), and the like are used as switching elements.

<Simulation Results>

FIG. 5 is a time change diagram of a current showing results of the circuit simulation model according to the first embodiment. FIG. 5 shows the results of circuit simulation relating to the PCS operation of the magnet of the embodiment. Since a switching frequency is as high as 10 kHz with respect to the time scale of energy supply of 0.1 seconds, the graph appears to be filled in, and the change in current disappears. From the envelope curve, it can be seen that the time constant attenuation characteristics are determined by the capacitance of the capacitor bank CA and the electric resistance of the heater circuit, and the time constant is approximately 24 msec, which is the same as the DC operation.

It can be seen that the current shunting to the PCS superconducting windings of the main coil 1 and the PCS 2 (leakage current to main coil, leakage current to PCS) is on the order of μA (almost zero) and 1A, respectively, while the current to the heater at time zero is 700 A, such that the current shunting can be almost ignored, and most of the energy in the capacitor bank CA is supplied to the heater (PCS heater).

FIG. 6 is a configuration diagram showing a superconducting magnet device 20A according to the first embodiment. FIG. 6 shows the configuration of the superconducting magnet device based on FIGS. 3 and 4. In FIG. 6, the main coil 1 as a superconducting coil, the PCS 2, the PCS heater winding 11 as a heater, and the blocking capacitor 13 are disposed in the cryostat 10. The excitation power supply 4 is electrically connected to the main coil 1 and the PCS 2 (persistent current switch) via the current lead 8, and the PCS 2 includes the PCS heater winding 11 (heater) and the PCS heater power supply 12 (heater driving power supply) for transitioning from a super-conduction state to a normal conduction state. The PCS heater power supply 12 is configured by the capacitor bank CA and the full bridge circuit of switching elements (switches SW1, SW2, SW3, and SW4). The current supplied from the PCS heater power supply 12 to the PCS heater winding 11 flows to the PCS heater winding 11 via the current lead 8. In FIG. 6, the connection point of the blocking capacitor 13 to the current lead 8 does not have to be the tip end of the current lead 8, and may be connected in the middle of the current lead 8. Similarly, the connection point of the PCS heater winding 11 to the current lead 8 does not have to be the tip end of the current lead 8, and may be connected in the middle of the current lead 8. To excite the main coil 1, it is necessary to realize the off state of the PCS 2 steadily. However, a steady-state heater installed in the PCS 2 for such purpose and a heater power supply for driving the heater are omitted.

In the superconducting magnet device 20A of the embodiment, provided is the capacitor bank CA in which a heater is installed in the superconducting winding portion for making the superconducting winding portion of the persistent current switch transition to a normal conduction state, and energy for driving the heater is stored, and a part of the electric circuit for supplying power from the capacitor bank CA to the heater is configured to share the low resistance current lead of the superconducting magnet excitation circuit. As a result, the superconducting winding can be transitioned to a normal conduction state at high speed, and the superconducting magnet device can be broken at high speed.

Second Embodiment

In the first embodiment, the heater driving method of the PCS 2 is shown, but in the second embodiment, use as a quench heater for preventing quenching of drive mode magnets without the PCS 2 will be described.

<Quenchback of REBCO Magnet>

Magnet protection by a quench heater is used for low temperature superconducting magnets with a large amount of storedenergy, but for oxide superconducting magnets with a slow quench propagation speed, it may be necessary to prevent superconducting burnout when an abnormal voltage occurs, regardless of the amount of storedenergy. Since the oxide superconductor has a high critical temperature, a large amount of energy is required to put the oxide superconducting coil winding in a normal state (resistive state), and thus the heater energy supply method shown in the first embodiment is effective. Note that REBCO is an abbreviation indicating a copper oxide superconductor having a composition formula represented by $REBa_2Cu_3O_x$ (RE is a rare earth element).

FIG. 7 is a circuit diagram showing a superconducting magnet device 20B according to a second embodiment. FIG. 8 is a configuration diagram showing the superconducting magnet device 20B according to the second embodiment. A superconducting magnet having a quench heater 14 will be described with reference to FIGS. 7 and 8.

The quench heater 14 (heater) is installed to raise the temperature of the superconducting coil windings in the same manner as that of the heater installed to raise the temperature of the PCS winding portion. A current supplied to the quench heater 14 from a quench heater power supply 15 (heater driving power supply) flows via at least a part of the current lead 8 to the heater. In a low temperature superconducting magnet with a high quench propagation speed, the heater may be attached to a part of the superconducting winding, but in a high temperature superconducting magnet with a low quench propagation speed, it is preferable to dispose the heater over the entire superconducting coil winding. For example, in NON PTL 2, a heater made of stainless steel is inserted between pancake coils of an oxide superconducting magnet configured by laminated pancake coils.

The quench heater power supply 15 is configured by the capacitor bank CA and the full bridge circuit of switching elements (switches SW1, SW2, SW3, and SW4). The method of supplying the heater energy from the capacitor bank CA has the advantage that the heater power supply can be configured at a lower cost than using a battery or the like, and the energy can be supplied at a higher speed. Since only the amount of energy stored in the capacitor bank CA is supplied to the heater, the burnout prevention circuit (control of amount of supplied energy) of the heater itself is not needed compared to an active power supply such as a battery or a power supply device, thus more preferable.

In a superconducting magnet device 20B of the embodiment, provided is the capacitor bank CA in which a heater is installed in the superconducting winding portion for making the superconducting winding portion transition to a normal conduction state, and energy for driving the heater is stored, and a part of the electric circuit for supplying power from the capacitor bank CA to the heater is configured to share the low resistance current lead of the superconducting magnet excitation circuit. As a result, the superconducting winding can be transitioned to a normal conduction state at high speed, and burnout of the superconducting winding can be prevented.

An electromagnet device of the present invention can be applied to a high temperature superconducting persistent current mode magnet in general, and particularly to an MRI device and an NMR device. The electromagnet device can be used for quench protection of high temperature superconducting magnets regardless of a drive mode operation or a persistent current mode operation.

REFERENCE SIGNS LIST

1: Main coil (superconducting coil, superconducting electromagnet)
2: PCS (persistent current switch)
3: PCS heater winding (PCS heater, heater)
4: Excitation power supply (DC power supply)
5: Protection resistor
6: Circuit breaker
7: PCS heater power supply
8: Current lead
10: Cryostat
11: PCS heater winding (PCS heater, heater)
12: PCS heater power supply (heater driving power supply)
13: Blocking capacitor (capacitor)
14: Quench heater (heater)
15: Quench heater power supply (heater driving power supply)
20, 20A, 20B: Superconducting magnet device
CA: Capacitor bank
SW1, SW2, SW3, SW4: Switch

The invention claimed is:

1. A superconducting magnet device comprising a superconducting coil in which a superconducting wire material is wound, and a persistent current switch electrically connected in parallel with the superconducting coil with respect to an excitation power supply for the superconducting coil, wherein
the excitation power supply is electrically connected to the superconducting coil and the persistent current switch via a current lead,
the persistent current switch is provided with a heater and a heater driving power supply for transitioning from a super-conduction state to a normal conduction state, and
a current supplied to the heater from the heater driving power supply flows to the heater via at least a part of the current lead.

2. The superconducting magnet device according to claim 1, wherein
the heater driving power supply is configured by a capacitor bank.

3. The superconducting magnet device according to claim 1, wherein
a capacitor for preventing a DC current is inserted in series in a heater circuit installed in the persistent current switch.

4. The superconducting magnet device according to claim 1, wherein
the heater driving power supply is an AC power supply.

5. The superconducting magnet device according to claim 4, wherein
the heater driving power supply is configured by a capacitor bank and a full bridge circuit of switching elements.

6. The superconducting magnet device according to claim 1, wherein
the superconducting wire material is a high temperature superconductor.

7. An NMR device comprising:
the superconducting magnet device according to claim 1.

8. An MRI device comprising:
the superconducting magnet device according to claim 1.

9. A superconducting magnet device comprising a superconducting coil in which a superconducting wire material is wound, an excitation power supply for exciting the superconducting coil, and a current lead electrically connecting the superconducting coil and the excitation power supply, wherein
a winding of the superconducting wire material is provided with a heater and a heater driving power supply for partially or entirely transitioning from a super-conduction state to a normal conduction state, and
a current supplied to the heater from the heater driving power supply flows to the heater via at least a part of the current lead.

10. The superconducting magnet device according to claim 9, wherein
the heater driving power supply is configured by a capacitor bank.

11. The superconducting magnet device according to claim 9, wherein
a capacitor for preventing a DC current is inserted in series in a heater circuit including the heater.

12. The superconducting magnet device according to claim 9, wherein
the heater driving power supply is an AC power supply.

13. The superconducting magnet device according to claim 12, wherein
the heater driving power supply is configured by a capacitor bank and a full bridge circuit of switching elements.

14. The superconducting magnet device according to claim 9, wherein
the superconducting wire material is a high temperature superconductor.

15. An NMR device comprising:
the superconducting magnet device according to claim 9.

16. An MRI device comprising:
the superconducting magnet device according to claim 9.

* * * * *